United States Patent [19]

McMillan et al.

[11] Patent Number: 5,300,281
[45] Date of Patent: Apr. 5, 1994

[54] RADIOLABELED COMPOSITIONS CONTAINING A CALCIFIC MATRIX AND THEIR USE FOR TREATMENT OF ARTHRITIS

[75] Inventors: Kenneth McMillan, Richwood; Jaime Simon, Angleton, both of Tex.

[73] Assignee: The Dow Chemical Company, Midland, Mich.

[21] Appl. No.: 906,998

[22] Filed: Jul. 1, 1992

Related U.S. Application Data

[63] Continuation-in-part of Ser. No. 656,397, Feb. 15, 1991, Pat. No. 5,137,709.

[51] Int. Cl.$^5$ .................. A61K 43/00; A61M 36/14; A61N 5/00
[52] U.S. Cl. ............................. 424/1.29; 600/4
[58] Field of Search .................... 424/1.1, 9, 489, 499; 534/10; 423/49, 50

[56] References Cited

U.S. PATENT DOCUMENTS

| | | | |
|---|---|---|---|
| 3,663,685 | 5/1972 | Evans | 424/1 |
| 3,784,453 | 1/1974 | Dworkin et al. | 204/131 |
| 3,863,004 | 1/1975 | Wolfangel | 424/1 |
| 4,057,616 | 11/1977 | Wolfangel | 424/1 |
| 4,454,106 | 6/1984 | Gansow et al. | 424/1.1 |
| 4,501,754 | 2/1985 | Wechter et al. | 514/456 |
| 4,752,464 | 6/1988 | Lieberman et al. | 424/1.1 |
| 4,758,429 | 7/1988 | Gordon | 424/85 |
| 4,789,501 | 12/1988 | Day et al. | 252/645 |
| 4,790,954 | 12/1988 | Burba, III et al. | 252/315.5 |
| 4,849,209 | 7/1989 | Lieberman et al. | 424/1.1 |
| 4,889,707 | 12/1989 | Day et al. | 424/1.1 |
| 4,897,254 | 1/1990 | Simon et al. | 424/1.1 |
| 4,898,724 | 2/1990 | Simon et al. | 424/1.1 |
| 4,906,450 | 3/1990 | Lieberman et al. | 424/1.1 |
| 4,915,932 | 4/1990 | McLaren et al. | 424/1.1 |
| 4,942,036 | 7/1990 | Geho et al. | 424/425 |
| 4,970,062 | 11/1990 | Atcher et al. | 424/1.1 |
| 5,066,478 | 11/1991 | Simon et al. | 424/1.1 |
| 5,133,956 | 7/1992 | Garlich et al. | 424/1.1 |
| 5,137,709 | 8/1992 | Simon et al. | 424/1.1 |
| 5,204,085 | 4/1993 | VanDeripe | 424/4 |

OTHER PUBLICATIONS

D. J. Hnatowich et al., "Dysprosium-165 Ferric Hydroxide Macroaggregates for Radiation Synovectomy", *The Journal of Nuclear Medicine*, 19(3), 303–308 (1977).

Maria Neves et al., "Palladium-109 and Holmium-166 Potential Radionuclides for Synoviotherapy-Radiation," etc., *Appl. Radiat. Isot.*, 38(9), 745–749 (1987).

Clement B. Sledge et al., "Experimental Radiation Synovectomy by Dy-165 Ferric Hydroxide Macroaggregate", *Arthritis and Rheumatism*, 20(7), 1334–1342 (Sep.-Oct. 1977).

Clement B. Sledge et al., "Intra-articular Radiation Synovectomy", *Clinical Orthopedics and Related Research*, No. 182, 37–40 (Jan.-Feb. 1984).

Clement B. Sledge et al., "Treatment of Rheumatoid Synovitis of the Knee with Intra-articular, etc.", *Arthritis and Rheumatism*, 29(2), 153–159 (Feb. 1986).

Pieter F. M. J. Spooren et al., "Synovectomy of the Knee with Y-90", *Nuclear Medicine*, 441–445 (1985).

Leonard Rosenthall, "Use of Radiocolloids for Intra-articular Therapy for Synovitis", Chapter 12 in *Therapy in Nuclear Medicine*, Richard P. Spencer Editor, 147–153, published by Grune and Stratton, N.Y. 1978.

*Primary Examiner*—Robert L. Stoll
*Assistant Examiner*—Lara E. Chapman

[57] ABSTRACT

Radioactive compositions containing a calcific matrix and methods for using the compositions for therapeutic radiation treatment including rheumatoid arthritis are disclosed.

46 Claims, No Drawings

RADIOLABELED COMPOSITIONS CONTAINING A CALCIFIC MATRIX AND THEIR USE FOR TREATMENT OF ARTHRITIS

CROSS-REFERENCE TO RELATED APPLICATION

This application is a continuation-in-part of U.S. Ser. No. 07/656,397, filed Feb. 15, 1991, issued as U.S. Pat. No. 5,137,709.

FIELD OF THE INVENTION

This invention relates to radioactive compositions containing a calcific matrix and use of these compositions in treating arthritis and other diseases.

BACKGROUND OF THE INVENTION

Rheumatoid arthritis is a prevalent disease characterized by chronic inflammation of the synovial membrane lining the afflicted joint. Current treatment methods for severe cases of rheumatoid arthritis include the removal of the synovial membrane, e.g., synovectomy. Surgical synovectomy has many limitations including the risk of the surgical procedure itself, and the fact that a surgeon often cannot remove all of the membrane. The diseased tissue remaining may eventually regenerate, causing the same symptoms which the surgery was meant to alleviate.

Radiation synovectomy is radiation-induced ablation of diseased synovial membrane tissue accomplished by injecting a radioactive compound into the diseased synovium. Early attempts to perform radiation synovectomy were hampered by an instability of the radioactive compositions utilized and by leakage of such compounds from the synovium into surrounding healthy tissues. The instability of labile radionuclide-complexes resulted in displacement of the radionuclide from the colloid complex and retention of the radionuclide in soft tissues. Significant leakage of the radioactive compound from the injection site exposed normal tissues to dangerous levels of radiation. Because of these limitations, new radiolabeled compositions were sought which would have minimal leakage.

U.S. Pat. Nos. 4,752,464; 4,849,209 and 3,906,450 describe compositions comprising a radioactive colloid in which a radionuclide is entrapped within an iron hydroxide matrix. The radioactive colloids are useful in radiation ablation procedures, for example, ablation of a synovium in rheumatoid arthritis. However, the use of radioactive colloids may still result in significant leakage of radioactivity from a site of injection, e.g., a synovium, and into the surrounding normal tissues, exposing normal tissues to an undesirable amount of radiation. To compensate for the leakage, a radioactive metal having a short half-life, such as [165]dysprosium (Dy-165) with a half-life of 2.3 hours, has been proposed for use as the therapeutic radionuclide. Because of its short half-life, the majority of Dy-165 radioactivity decays before significant leakage can occur, thereby minimizing the dose of radiation to normal tissues.

The use of radioactive metals having a short half-life severely limits the utility of the therapeutic radiation procedure in two significant ways. First, radioactive compositions prepared with short half-life isotopes lose a significant amount of radioactivity because of decay during shipment to distant locations. Second, to achieve a therapeutic dose of a composition comprising a radioactive metal having a short half-life, large amounts of radioactive materials must be used. As a result, clinical personnel must handle large amounts of radioactive materials.

Therefore, there remains a need for a therapeutic radioactive composition which upon injection into a synovium, would remain at the site of injection, e.g., within a synovium, for a prolonged period of time. Prolonged retention at the site of injection would allow use of radionuclides having a longer half-life in therapeutic procedures, including radiation synovectomy, without fear of significant leakage from the site of injection and radiation exposure to normal tissues.

SUMMARY OF THE INVENTION

The present invention discloses a therapeutic radiation ablation treatment method comprising injecting a patient with a therapeutically effective amount of a composition comprising in a pharmaceutically-acceptable carrier a radionuclide sorbed to a calcific matrix.

The present invention also provides a therapeutic radiation ablation treatment method comprising injecting a patient with a therapeutically effective amount of a composition comprising in a pharmaceutically-acceptable carrier a radionuclide, a calcific matrix and a layered mixed metal hydroxide (LMMH) of the formula:

$$Li_m D_d T(OH)_{(m+2d+3+na)} A_a^n \qquad (I)$$

where:
- m represents the number of Li ions present;
- D represents divalent metal ions;
- d is the number of ions of D in the formula;
- T represents trivalent metal ions;
- A represents monovalent or polyvalent anions other than OH ions;
- a is the number of ions of A in the formula;
- n is the valence of A; and
- (m+2d+3+na) is equal to or greater than 3.

In another aspect, the present invention provides a therapeutic radiation ablation treatment method comprising injecting a patient with a therapeutically effective amount of a composition comprising in a pharmaceutically acceptable carrier a chelate sorbed to a calcific matrix, wherein the chelate is a radionuclide complexed with a chelating agent.

In yet another aspect, the present invention provides a therapeutic radiation ablation treatment method comprising injecting a patient with a therapeutically effective amount of a composition comprising in a pharmaceutically acceptable carrier a chelate sorbed to a calcific matrix; and a layered mixed metal hydroxide as defined by Formula I, wherein the chelate is a radionuclide complexed with a chelating agent.

When the compositions containing a radionuclide sorbed to calcific matrix or a radionuclide and calcific matrix with the additional LMMH and/or chelating agent are injected into the synovium of a subject for the treatment of rheumatoid arthritis, they are retained at the site of injection for a prolonged period of time without significant leakage of radioactivity. The low loss of radioactivity from the desired site minimizes the radiation exposure to normal tissue.

DETAILED DESCRIPTION OF THE INVENTION

As used herein, the terms "chelating agent" or "ligand" mean a compound capable of chelating or sequestering a metal ion. The term "chelate" means a chelating agent which has sequestered a metal ion. The chelation or sequestering of a metal ion by a chelating agent is also referred to herein as "complexation" or the metal ion being "complexed" with the chelating agent.

In one method of the present invention it has been found that compositions comprising a radionuclide sorbed to a calcific matrix will remain in a patient near the site of injection. By remaining near the site of injection, such compositions are suitable for radiation ablation treatments. For example, in the treatment of arthritis, particularly rheumatoid arthritis, when the composition is injected into the synovium of the patient, the composition remains substantially within the synovium.

In another method of the present invention, a LMMH is added to radiolabeled calcific matrix to stabilize the radiolabeled calcific matrix. A stabilized radiolabeled calcific matrix is useful for therapeutic radiation ablation treatment methods, such as for the treatment of arthritis.

Stabilization includes the prevention of leakage of the radioactive composition from a site of injection into surrounding normal tissues. When treating rheumatoid arthritis, such stabilization prevents significant leakage from the synovial cavity.

A "calcific matrix" means a complex of calcium to which metals will sorb, such as, for example, calcium phosphate, calcium carbonate or calcium oxalate. A preferred calcific matrix is a complex phosphate of calcium such as hydroxyapatite, represented by the formula

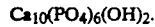

$Ca_{10}(PO_4)_6(OH)_2$.

As used herein, the term calcific matrix includes modifications of the matrix surface which do not substantially affect the ability of the calcific matrix to sorb metal ions. For hydroxyapatite, such modifications include the presence of ions such as carbonate, magnesium, or citrate at the hydroxyapatite surface and substitution of other elements, such as carbon for potassium; magnesium, sodium, or potassium for calcium; and fluoride for hydroxy. Calcific matrices for use in the present invention are readily available from commercial sources.

The calcific matrices used in the present invention are particulate in nature, the particles being spherical or irregular in form having an average diameter of between about 1 and about 90 microns. Preferably the particles have a diameter of between about 5 and about 75 microns. More preferably the particles have a diameter between about 5 and about 50 microns.

Radionuclides useful in the present invention include those having therapeutic efficacy, for example, in radiation ablation therapies such as radiation synovectomy. Preferably the radionuclides are beta emitting metals with half-lives of from about 2 hours to about 7 days. Examples of such metals include holmium (Ho-166), samarium (Sm-153), rhodium (Rh-105), lutetium (Lu-177), indium (In-115m), dysprosium (Dy-165), yttrium (Y-90), lanthanum (La-140), gadolinium (Gd-159), ytterbium (Yb-175), rhenium (Re-186), (Re-188) and scandium (Sc-47). More preferred are the radionuclides Ho-166, Sm-153, Re-186, Re-188, Rh-105, Lu-177, In-115 m, and Dy-165. Most preferred are the radionuclides Ho-166, Sm-153, Re-186 and Re-188.

The respective radionuclides can be produced by methods known in the art. For example, in a nuclear reactor, a nuclide is bombarded with neutrons to obtain a nuclide with additional neutrons in its nucleus. For example:

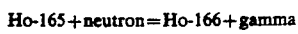

Ho-165 + neutron = Ho-166 + gamma

Typically, the desired radionuclide can be prepared by irradiating an appropriate target, such as a metal oxide. Another method of obtaining radionuclides is by bombarding nuclides with particles in a linear accelerator or cyclotron. Yet another way of obtaining radionuclides is to isolate them from fission product mixtures.

Binding of the radionuclide to the calcific matrix can be accomplished by exposing the metal to an aqueous suspension of the calcific matrix at a pH of about 3 to about 12, preferably about 4 to about 9. The use of the terms "binding" or "bound" to the calcific matrix mean that the metal is sorbed to the calcific matrix and remains associated with the calcific matrix due to Van der Waal's forces, hydrogen, ionic or covalent bonding.

Layered mixed metal hydroxides are preferably prepared by an instantaneous ("flash") coprecipitation wherein soluble metal compounds, e.g., salts of the metals, are intimately mixed (using non-shearing agitation or mixing) with an appropriate alkaline material which supplies hydroxyl groups to form the mixed metal hydroxide crystals. A distinguishing feature of the composition is that the crystals are essentially a monolayer, that is, one layer of the mixed metal hydroxide per unit cell of the crystal. These are termed "monodispersed" crystals when they are in a liquid carrier and are individual crystals of monolayer mixed metal hydroxides. (See EPO No. 0,207,811, U.S. Pat. Nos. 4,664,843 and 4,790,954.)

In the above Formula I, m may be from 0 to about 1, and most preferably m is 0.5 to about 0.75 when not 0. The D metal may be Mg, Ca, Ba, Sr, Mn, Fe, Co, Ni, Cu, Zn, and most preferably D is Mg, Ca, or mixtures of these. The value of d may be from 0 to about 4, provided that both m and d are not 0, and preferably the value of d is from about 1 to about 3 and most preferably about 1. The T metal is preferably trivalent, and may be Al, Ga, Cr, or Fe; preferably T is Al or Fe, and most preferably T is Al. The A anions may be monovalent or polyvalent, including divalent and trivalent, and they may be inorganic ions such as halide, sulfate, nitrate, phosphate, carbonate. Preferably the A anions are halide, sulfate, phosphate or carbonate or they may be hydrophilic organic ions such as glycolate, lignosulfonate, polycarboxylate or polyacrylate. These anions often are the same as the anions which form part of the metal compound precursors from which these crystals are formed. Since "n" is a negative number, "na" is also a negative number.

Methods for preparing a LMMH useful in the present invention, are disclosed in U.S. Pat. No. 4,790,945 to Burba et al., the disclosure of which is hereby incorporated by reference. To produce LMMH, according to the Burba et al. method, a mixture of the selected soluble metal compounds, especially the acid salts (e.g., chloride, nitrate, sulfate, phosphate, etc.), are dissolved in an aqueous carrier. The ratios of the metal ions in the solution are predetermined to give the ratios desired in the final product. The concentration limit of the metal compounds in the solution is governed in part by the saturation concentration of the least soluble of the metal compounds in the solution. Any non-dissolved portion of the metal compounds may remain in the final product as a separate phase. This is usually not a serious problem if the concentration of such separate phase is a relatively low amount in comparison to the soluble portions, and preferably is not more than about 20 percent of the amount of the soluble portions. The solution is then mixed rapidly and intimately with an alkaline source of $OH^-$ ions while substantially avoiding shearing agitation thereby forming monodispersed crystals of LMMH. One convenient way of achieving such mixing is by flowing the diverse feed streams into a mixing tee from which the mixture flows, carrying the reaction product, including the monodispersed LMMHs of the above Formula I. The mixture may then be filtered, washed with fresh water to remove extraneous soluble ions (such as $Na^+$, $NH^{+4}$ ions, and other soluble ions) which are not part of the desired product.

A preferred method of preparing the Formula I LMMH composition, is to react a solution of metal salts, preferably magnesium and aluminum salts (approximately 0.25 molar), with an appropriate base such as ammonium or sodium hydroxide in quantities sufficient to precipitate the LMMH. For ammonium hydroxide, the preferably range is between 1 and 1.5 equivalents of $OH^-$ per equivalent of anion.

The precipitation should be done with little or no shear so that the resultant flock is not destroyed. One method of accomplishing this is to flow two streams, the salt stream and the base stream, against one another so that they impinge in a low shear converging zone such as would be found in a mixing tee. The reaction product is then filtered and washed, producing a filter cake of about 10 percent solids. (See European Patent Application No. 02 07 811).

The LMMH crystals have a positive charge associated with the surface of the LMMH crystals, and are consequently less readily dispersed in non-polar than in polar fluids. It may be desirable to modify the LMMH to render it more readily dispersed in the fluid of choice. Such modification may be accomplished, for example, by treating the LMMH crystals, for example, with an aliphatic carboxylic or fatty acid, such as stearic acid.

The radiolabeled calcific matrix stabilized with LMMH are generally prepared by mixing the radiolabeled calcific matrix with LMMH. The calcific matrix may be radiolabeled prior to or simultaneously with the LMMH mixing step. In general, the calcific matrix will be in suspension and the LMMH may be added in solid form, or in suspension. The amount of LMMH in the final composition will vary with the intended use, and will be that amount which is effective in reducing leakage of radioactivity from a site of injection of the composition. Generally the amount of LMMH in the final composition will be in the range of from about 1 weight percent to about 20 weight percent of the total composition.

Another method of the present invention provides a composition comprising in a pharmaceutically acceptable carrier a chelating agent, a radionuclide and a calcific matrix for use in radiation ablation treatments, especially in the treatment of rheumatoid arthritis. The chelating agent, radionuclide, calcific matrix composition can be stabilized by the addition of a layered mixed metal hydroxide. When a chelating agent is used. The metal is first complexed by the chelating agent to form a chelate, and then the chelate sorbed to the calcific matrix. Such composition may be particularly advantageous if leakage from the site of injection occurs as some or all of the chelate may be eliminated from the body. Thus, should the chelate migrate from the site of injection, the radionuclide can be directed away from non-target tissues.

Chelating agents known in the art can be used in the present invention. Preferred chelating agents with radionuclides having rare earth type chemistry are polyaminophosphonates. Preferred chelating agents with Re-186 and Re-188 are diphosphonate chelating agents. Examples of diphosphonate chelating agents are those disclosed in U.S. Pat. Nos. 4,606,907 and 4,515,767, the disclosures of which are hereby incorporated by reference, and include, for example, methlenediphosphonic acid, hydroxyethanediphosphonic acid and hydroxymethylene-diphosphonic acid.

Cyclic polyaminophosphonate chelating agents useful in the present invention include, for example, 1,4,7,10-tetraazacyclododecane-1,4,7,10-tetramethylenephosphonic acid and analogs disclosed in U.S. Pat. No. 4,882,142, the disclosure of which is hereby incorporated by reference, and the polyamino phosphonates disclosed in U.S. patent application Ser. No. 07/565,379, filed Aug. 9, 1990, the disclosure of which is hereby incorporated by reference; 1,3-propanediamine-N-(carboxypropyl)-N,N',N'-trimethylenephosphonic acid, ethylenediamine-N-(4-aminophenethyl)-N,N',N', -trimethylenephosphonic acid, ethylenediaminetetramethylenephosphonic acid, 1-(carboxy)ethylenediaminetetramethylenephosphonic acid, 1-(4-aminobenzyl)ethylenediaminetetramethylenephosphonic acid, N'''-(4-aminophenyl)-dipropylenetriamine-N',N',N''',N'''-tetramethylenephosphonic acid and N''-(4-aminophenethyl)-diethylenetriamine-N'N',N''',N'''-tetramethylenephosphonic acid being representative of the polyamine phosphonates in U.S. patent application Ser. No. 07/565,379.

Linear polyamino phosphonates, useful in the present invention include, for example, ethylenediaminetetramethylene-phosphonic acid (EDTMP), diethylenetriaminepentamethylenephosphonic acid (DTPMP), hydroxyethylethylenediaminetrimethylenephosphonic acid (HEEDTMP), nitrilotrimethylenephophonic acid (NTMP), tris(2-aminoethyl)aminehexamethylenephosphonic acid (TTHMP), 1-carboxyethylenediaminetetramethylenephosphonic acid (CEDTMP), bis(aminoethylpiperazine)tetramethylenephosphonic acid (AEPTMP), N-methylethylenediaminetrimethylenephosphonic acid (MEDTMP), N-isopropylethylenediaminetrimethylenephosphonic acid (IEDTMP) and N-benzylethylenediaminetrimethylenephosphonic acid (BzEDTMP) as disclosed in patent application Ser. No. 07/629,894, the disclosure of which is hereby incorporated by reference.

The aminophosphonate chelating agents can be prepared by a number of known synthetic techniques. Of particular importance is the reaction of a compound containing at least one reactive amine hydrogen with a carbonyl compound (aldehyde or ketone) and phosphorous acid or dervative thereof as described in U.S. Pat. No. 3,288,846 and described by Moeritzer and Irani, *J. Org. Chem.*, 31, 1603 (1966), the disclosures of which are hereby incorporated by reference.

Complexation of a metal ion by the chelating agent can be accomplished by contacting the chelating agent with an aqueous solution of the metal ion at a pH of about 3 to about 12, preferably about 4 to about 9. In general, the chelating agents used in the present invention are capable of complexing one metal cation per molecule of chelating agent. Thus the molar ratio of chelating agent to metal ion will be about 1 to 1. In many cases, extra ligand will be needed to complex all of the metal. Thus for some systems, the ligand to metal ratio will be greater than 1 to 1.

When a chelate is used, the radionuclide is preferably complexed by the chelating agent prior to sorption of the chelate by the calcific matrix. Sorption of the chelating agent, followed by addition of the radionuclide can also be done. However, the latter procedure may result in some sorption of the radionuclide by the calcific matrix as well as sequestration by the chelating agent.

The addition of a LMMH to a chelate sorbed to calcific matrix can be prepared as previously described for addition of a LMMH to a radiolabeled calcific matrix.

The pharmaceutical formulations of the present invention contain radioactive metals sorbed to calcific matrix; radioactive metal sorbed to calcific matrix and stabilized by a LMMH; a chelate sorbed to a calcific matrix; or a chelate sorbed to calcific matrix and stabilized by a LMMH in a physiologically acceptable carrier. Examples of suitable physiologically acceptable carriers include, for example, aqueous carriers such as phosphate buffered saline, glycols or saline. The pharmaceutical formulations can be administered to a patient for therapeutic treatment by methods known in the art, e.g., intra-articularly or by injection. For example, a hydroxyapatite-$^{153}$Sm-LMMH formulation may be prepared in saline and injected into a joint for radiation synovectomy.

The formulations of the present invention are in solid or liquid form. These formulation may also be in kit form such that the various components are mixed at the appropriate time prior to use. Whether premixed or as a kit, the formulations usually require a pharmaceutically acceptable carrier. The formulations can also be made in a kit form, wherein the components of the formulation with the exception of the radionuclide are placed in a vial and the radionuclide added prior to use.

The quantity of the radioactive composition administered to the patient will depend upon several factors including the specific radionuclide, its specific activity and emissions, the particular type of therapeutic treatment, e.g., type of injection site, duration of therapy desired, and type of disease being treated, and the amount of radioactivity desired at the site of injection.

A therapeutic dosage of radioactivity is that which is sufficient when administered to a patient, to achieve the therapeutic radiation ablation result, for example, the amount sufficient, when injected into the synovium of a patient, to ablate the synovial membrane. In general, the therapeutic dosage will be that which delivers approximately 5 Gy to 1,500 Gy. A more preferred dosage is that which delivers from about 20 Gy to about 500 Gy to the site of injection. Gy is Greys wherein 1 Gy equals 100 rads.

The invention will be further clarified by a consideration of the following examples, which are intended to be purely exemplary of the present invention.

EXAMPLES

EXAMPLE 1 Preparation of a Layered Mixed Metal Hydroxide (LMMH)

A LMMH was prepared according to the method of Burba, disclosed in U.S. Pat. No. 4,790,954. In general, a solution of $MgCl_2 \cdot AlCl_3$ (each 0.25M) is pumped into one arm of a mixing tee. Ammonium hydroxide is pumped into a second, opposite arm of the tee so that the two solutions met in the tee. The coprecipitation product is poured out of the third arm and into a beaker, and consists essentially of delicate flocs of monosphores, monolayer, and microcrystals of LMMH, having the approximate formula $MgAl(OH)_{4.7}Cl_{0.3}$ suspended in an aqueous solution of ammonium chloride. The product is filtered, washed and drain-dried. The drain-dried LMMH crystals still contain some water.

EXAMPLE 2 Preparation of Hydroxyapatite/$^{153}$Sm Mixture

Hydroxyapatite (Type I, calcium phosphate hydroxide) was purchased from the Sigma Chemical Company as a 25 percent by weight solids in 0.001M phosphate buffer, pH 6.8. A portion of the HAP was centrifuged for five minutes at 4700 rpm in a clay-Adams safety head centrifuge) to form a moist pellet, and the excess buffer decanted. Approximately 1.0 mL of the HAP pellet was placed in a vial and 100 μL of a samarium working solution and 300 μL of water were added. The samarium working solution contained 2-3 μL of $^{153}$Sm, obtained from The University of Missouri Research Reactor, Columbia, Mo., added to 1 mL of 0.3 mM samarium chloride (obtained from Alrich Chemical Company, Inc.).

The HAP/samarium mixture was centrifuged for five minutes at 4,700 rpm in a Clay-Adams safety head centrifuge. The supernatant was decanted and determined to contain approximately 125, 724 count/minute (CPM) $^{153}$Sm. The counts remaining in the solids was found to be in excess of 20 million CPM indicating less than 0.1 percent of the $^{153}$Sm was unbound in the liquid phase.

EXAMPLE 3A Preparation of a HAP/$^{153}$SM/LMMH Mixture (Mixture A)

To a vial containing a 0.3 gm of the HAP/$^{153}$samarium mixture obtained as in Example 2 was added 0.3 g of a LMMH obtained as in Example 1. The mixture of HAP/$^{153}$Sm/LMMH was allowed to sit for 10 minutes before injection into the synovium of a rabbit.

EXAMPLE 3B (Mixture B)

A HAP/$^{153}$Sm/LMMH mixture was prepared as in Example 3A except 0.6 g of the LMMH were added.

EXAMPLE 4 Preparation of a EDTMP/$^{153}$Sm/LMMH

To a vial containing 34.43 mg of ethylenediaminetetramethylenephosphonic acid (EDTMP) was added 984.0 μL of a samarium working solution prepared as described in Example 2. This was followed by the addition of 30 μL of a 50 percent by weight solution of sodium hydroxide. The pH of the solution was then adjusted to between about 7 and about 8 by the addition of 10 μL of 12.5M hydrochloric acid. The amount of complexation as determined by using a cation exchange resin (Sephadex TM C-25, a trademark of Pharmacia, Inc.).

A 100 μL aliquot of the EDTMP/$^{153}$Sm complex was added to a 1 mL portion of a HAP pellet prepared as described in Example 2. The mixture was well mixed and then centrifuged for 10 minutes at 4,700 rpm in a Clayton-Adams safety head centrifuge and the supernatant decanted. It was determined that less than 0.1 percent of the radioactivity was in the supernatant, the remainder of the activity being associated with the HAP.

EXAMPLE 5 Use of Radiolabeled Compositions for Radiation Synovectomy

A 150 μL dose of the preparation obtained by the procedure of Example 2 were injected into the knee joint of an anesthetized rabbit. The syringe was disconnected from the needle, which was left in the joint, and the needle washed with 0.5 mL of 0.85 percent saline. The needle was then removed. The knee joint was stabilized and placed under a 3 inch NaI gamma detector (Canberra, Meriden, Conn.). At the end of an hour, after correcting for decay, no loss of radioactivity from the synovial cavity was observed. Repeating this procedure by injection into another knee joint, 0.5 percent loss of activity from the synovial cavity was observed in one hour.

Using the above procedure for injecting separate 150 μL doses of the preparations obtained by the procedures of Examples 3A and 3B, no leakage of radioactivity from the synovium was observed.

Using the above procedure for injecting a 150 μL dose of a preparation obtained by the procedure of Example 4, after 70 minutes, 99.4 percent of the original activity remained within the synovial cavity.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

What is claimed is:

1. A therapeutic radiation ablation treatment method comprising:
   injecting into the synovium of a patient a therapeutically effective amount of a pharmaceutical composition consisting essentially of a radionuclide sorbed to a calcific matrix, wherein the calcific matrix is particulate, the particles being spherical or irregular in form and having an average diameter of between about 1 and about 90 microns.

2. The method of claim 1 wherein the calcific matrix is hydroxyapatite.

3. The method of claim 1 wherein the patient is suffering from rheumatoid arthritis.

4. The method of claim 1 wherein the radionuclide is Sm-153, Ho-166, Lu-177, La-140, Gd-159, Yb-175, In-115m, Y-90, Sc-47, Re-186 or Re-188.

5. The method of claim 4 wherein the radionuclide is Sm-153 or Ho-166.

6. A therapeutic radiation ablation treatment method comprising:
   injecting into the synovium of a patient a therapeutically effective amount of a pharmaceutical composition comprising a radionuclide sorbed to a calcific matrix, wherein the calcific matrix is particulate, the particles being spherical or irregular in form and having an average diameter of between about 1 and about 90 microns and the composition further contains a layered mixed metal hydroxide of Formula I:

$$Li_m D_d T(OH)_{(m+2d+3+na)} A_a^n \qquad (I)$$

wherein:
m is 0 to about 1
D is a divalent metal ion selected from the group consisting of magnesium, calcium, barium, strontium, manganese, iron, cobalt, nickel, copper, and zinc or a mixture thereof;
d is 0 to about 4;
provided that both m and d are not 0;
T is a metal ion selected from the group consisting of aluminum, gallium, chromium, and iron;
A is a monovalent or polyvalent ion other than a hydroxyl ion;
n is the valence of the anion A; and
(m+2d+3+na) is equal to or greater than 3.

7. The method of claim 6 wherein the patient is suffering from rheumatoid arthritis.

8. The method of claim 6 wherein the calcific matrix is hydroxyapatite.

9. The method of claim 6 wherein the radionuclide is Sm-153, Ho-166, Lu-177, La-140, Gd-159, Yb-175, In-155m, Y-90, Sc-47, Re-186 or Re-188.

10. The method of claim 9 wherein the radionuclide is Sm-153 or Ho-166.

11. The method of claim 6 wherein m is in from about 0.5 to about 0.75; D is magnesium, calcium, or a mixture thereof; d is from about 1 to about 3; and T is a halide, sulfate, or phosphate.

12. The method of claim 6 wherein the layered mixed metal hydroxide has the formula:

$$Mg_x Al_y(OH)_z A_a^n$$

wherein:
x is approximately 1 to approximately 3;
y is approximately 1;
z is approximately 3 to approximately 5;
A is a halide, sulfate, phosphate, or carbonate;
n is the valence of A; and
a is approximately 0.1 to 1.0.

13. The method of claim 12 wherein x is 1, y is 1, z is 4.7 and a is 0.3.

14. The method of claim 12 wherein the radionuclide is Sm-153, Ho-166, Lu-177, La-140, Gd-159, Y6-175, In-115m, Y-90, Sc-47, Re-186 or Re-188.

15. The method of claim 14 wherein the radionuclide is Sm-153 or Ho-166.

16. A therapeutic radiation ablation treatment method comprising:
   injecting into the synovium of a patient a therapeutically effective amount of a pharmaceutical composition consisting essentially of a chelate sorbed to a calcific matrix, wherein the chelate is a radionuclide complexed with a chelating agent wherein the calcific matrix is particulate, the particles being spherical or irregular in form and having an average diameter of between about 1 and about 90 microns.

17. The method of claim 16 wherein the patient is suffering from rheumatoid arthritis.

18. The method of claim 16 wherein the calcific matrix is hydroxyapatite.

19. The method of claim 16 wherein the radionuclide is Sm-153, Ho-166, Lu-177, La-140, Gd-159, Y6-175, In-115m, Y-90, Sc-47, Re-186 or Re-188.

20. The method of claim 19 wherein the radionuclide is Sm-153 or Ho-166.

21. The method of claim 16 wherein the chelating agent is a polyaminophosphonate.

22. The method of claim 21 wherein the chelating agent is 1,4,7,10-tetraazacyclododecane-1,4,7,10-tetramethylenephosphonic acid or ethylenediaminetetramethylenephosphonic acid.

23. The method of claim 21 wherein the radionuclide is Ho-166 or Sm-153.

24. The method of claim 16 wherein the chelating agent is a diphosphonate.

25. The method of claim 24 wherein the chelating agent is methylenediphosphonic acid, hydroxyethanediphosphonic acid or hydroxymethylenediphosphonic acid.

26. The method of claim 24 wherein the radionuclide is Re-186 or Re-188.

27. The method of claim 16 wherein the composition further contains a layered mixed metal hydroxide of Formula I:

$$Li_m D_d T(OH)_{(m+2d+3+na)} A_a^n \qquad (I)$$

wherein:

m is 0 to about 1;

D is a divalent metal ion selected from the group consisting of magnesium, calcium, barium, strontium, manganese, iron, cobalt, nickel, copper, and zinc or a mixture thereof;

d is 0 to about 4;

provided that both m and d are not 0;

T is a metal ion selected from the group consisting of aluminum, gallium, chromium, and iron;

A is a monovalent or polyvalent ion other than a hydroxyl ion;

n is the valence of the anion A;

a is the number of anions A in the formula; and $(m+2d+3+na)$ is equal to or greater than 3.

28. The method of claim 27 wherein the patient is suffering from rheumatoid arthritis.

29. The method of claim 27 wherein m is in from about 0.5 to about 0.75;

D is magnesium, calcium, or a mixture thereof; d is from about 1 to about 3; and T is a halide, sulfate, or phosphate.

30. The method of claim 27 wherein the radionuclide is Sm-153, Ho-166, Lu-177, La-140, Gd-159, Y6-175, In-115m, Y-90, Sc-47, Re-186 or Re-188.

31. The method of claim 27 wherein the chelating agent is a polyaminophosphonate.

32. The method of claim 31 wherein the polyaminophosphonate is 1,4,7,10-tetraazacyclododecane-1,4,7,10-tetramethylenephosphonic acid or ethylenediaminetetramethylenephosphonic acid.

33. The method of claim 31 wherein the radionuclide is Ho-166 or Sm-153.

34. The method of claim 27 wherein the chelating agent is a diphosphonate.

35. The method of claim 34 wherein the chelating agent is methylenediphosphonic acid, hydroxyethanediphosphonic acid or hydroxymethylenediphosphonic acid.

36. The method of claim 35 wherein the radionuclide is Re-186 or Re-188.

37. The method of claim 27 wherein the layered mixed metal hydroxide has the formula:

$$Mg_x Al_y(OH)_z A_a^n$$

wherein:

x is approximately 1 to approximately 3;

y is approximately 1;

z is approximately 3 to approximately 5;

A is a halide, sulfate, phosphate, or carbonate;

n is the valence of A; and a is approximately 0.1 to 1.0.

38. The method of claim 37 wherein x is 1, y is 1, z is 4.7 and a is 0.3.

39. The method of claim 38 wherein the radionuclide is Sm-153, Ho-166, Lu-177, La-140, Gd-159, Y6-175, In-115m, Y-90, Sc-47, Re-186, or Re-188.

40. The method of claim 39 wherein the radionuclide is Sm-153 or Ho-166.

41. The method of claim 37 wherein the chelating agent is a polyaminophosphonate.

42. The method of claim 41 wherein the polyaminophosphonate is 1,4,7,10-tetraazacyclododecane-1,4,7,10-tetramethylenephosphonic acid or ethylenediaminetetramethylenephosphonic acid.

43. The method of claim 42 wherein the radionuclide is Ho-166 or Sm-153.

44. The method of claim 37 wherein the chelating agent is a diphosphonate.

45. The method of claim 44 wherein the chelating agent is methylenediphosphonic acid, hydroxyethanediphosphonic acid or hydroxymethylenediphosphonic acid.

46. The method of claim 45 wherein the radionuclide is Re-186 or Re-188.

* * * * *